(12) United States Patent
Miller

(10) Patent No.: US 7,846,094 B2
(45) Date of Patent: Dec. 7, 2010

(54) SYSTEM AND METHOD FOR NEUROLOGICAL INJURY DETECTION, CLASSIFICATION AND SUBSEQUENT INJURY AMELIORATION

(76) Inventor: Landon C. G. Miller, 325 Queen City Ave., Tuscaloosa, AL (US) 35401

(*) Notice: Subject to any disclaimer, the term of this patent is extended or adjusted under 35 U.S.C. 154(b) by 0 days.

(21) Appl. No.: 10/599,016

(22) PCT Filed: Mar. 17, 2005

(86) PCT No.: PCT/US2005/008907

§ 371 (c)(1),
(2), (4) Date: Sep. 18, 2006

(87) PCT Pub. No.: WO2005/089430

PCT Pub. Date: Sep. 29, 2005

(65) Prior Publication Data

US 2007/0208268 A1 Sep. 6, 2007

Related U.S. Application Data

(60) Provisional application No. 60/554,018, filed on Mar. 17, 2004.

(51) Int. Cl.
*A61B 5/00* (2006.01)

(52) U.S. Cl. .................................................. 600/301
(58) Field of Classification Search ................. 600/300, 600/554, 587, 547, 375, 382, 384, 301; 436/86; 514/263; 604/65, 891.1; 705/7; 564/92, 564/99
See application file for complete search history.

(56) References Cited

U.S. PATENT DOCUMENTS

| 5,364,793 | A | 11/1994 | Cameron, Sr. et al. |
| 5,958,933 | A | 9/1999 | Naftchi |
| 2001/0037083 | A1* | 11/2001 | Hartlaub et al. ............... 604/65 |
| 2002/0183647 | A1 | 12/2002 | Gozani et al. |
| 2004/0122719 | A1* | 6/2004 | Sabol et al. .................... 705/7 |
| 2004/0138502 | A1* | 7/2004 | Traynelis et al. .............. 564/92 |

* cited by examiner

Primary Examiner—Max Hindenburg
Assistant Examiner—Brian Szmal
(74) Attorney, Agent, or Firm—Gifford, Krass, Sprinkle, Anderson & Citkowski, P.C.

(57) ABSTRACT

A system (10) and method for detecting and analyzing neurological damage in an injured subject are provided using electrical nerve conduction analyses supported by a computing device (12). An appropriate neurologically protective pharmaceutical for that injury type and circumstances based on the result of said analyses is suggested.

11 Claims, 3 Drawing Sheets

SYSTEM AND METHOD FOR NEUROLOGICAL INJURY DETECTION, CLASSIFICATION AND SUBSEQUENT INJURY AMELIORATION

RELATED APPLICATION

This application claims priority of U.S. Provisional Patent Application Ser. No. 60/554,018 filed Mar. 17, 2004, which is incorporated herein by reference.

FIELD OF THE INVENTION

The present invention generally relates to the immediate treatment of neurological injuries. More specifically, the present invention relates to a system and method for actively and passively detecting and analyzing neurological damage in an injured person using electrical and chemical analyses supported by a computer system and database, selecting an appropriate neurologically protective pharmaceutical for that injury type and circumstances based on the result of said analyses, and then delivering this pharmaceutical via direct injection, intravenous delivery, or other means into the person using components of the kit of which all the elements of the invention are a part.

BACKGROUND OF THE INVENTION

There are approximately 500,000 new cases of Traumatic Brain Injury (TBI) admitted to hospitals in the United States each year, and the incidence requiring hospitalization is estimated to be approximately 200 to 225 per 100,000 population. Currently, it is estimated that brain injuries account for 12% of all hospital admissions in the United States. Spinal Cord Injuries (SCI) account for another 10,000 cases per year.

Transportation-related injuries of all types are responsible for approximately 50% of TBI within the United States and the developed world. The costs of severe TBI to the individual, family, and society are extremely high. Extrapolation of the data from studies results in an estimated 26,000 trauma deaths per year, with another 20,000 to 45,000 patients suffering significant physical or neurobehavioral sequelae resulting in functional loss. The direct costs of TBI are over $25 billion annually in the United States alone. The average direct hospital charges were estimated to be $117,000 per admission in 1993 within the Traumatic Brain Injury Model Systems. One can easily determine that TBI is an extraordinary medical care problem globally that is closely comparable in morbidity, mortality, and economic loss to human immunodeficiency virus infection; yet it is an understudied mechanism of morbidity and mortality.

Currently, there exists no system, process or method for treating such injuries at the scene of such incidents except for rudimentary techniques such as immobilization and physical stabilization. While helpful, research has shown that cell death in the brain and spinal cord starts almost immediately. It is estimated that 40% of all damage is done in the first ten minutes after injury and most initial damage is done in four hours. Yet there is no present system or method for at least ameliorating such damage inside the treatment time window.

Accordingly, it would be advantageous and desirable to have a system and method of detecting and analyzing neurological injuries and providing immediate, ameliorating treatment while overcoming the drawbacks and disadvantages of any somewhat related prior art.

SUMMARY OF THE INVENTION

According to the present invention, there is disclosed a system and method for detecting and analyzing neurological damage in an injured subject using nerve conduction analyses supported by a computing device. A measured electrical signal is compared to a reference value computed based on a mathematical equation or stored within a database accessible by the computing device. The electrical signal is generated by placing an emitter and a detector in communication by a subject nerve path, the signal indicative of conduction via the nerve path. A neurologically active pharmaceutical kit provides for immediate treatment to inhibit secondary neuronal damage.

DETAILED DESCRIPTION OF THE PREFERRED EMBODIMENTS

Figure 1:
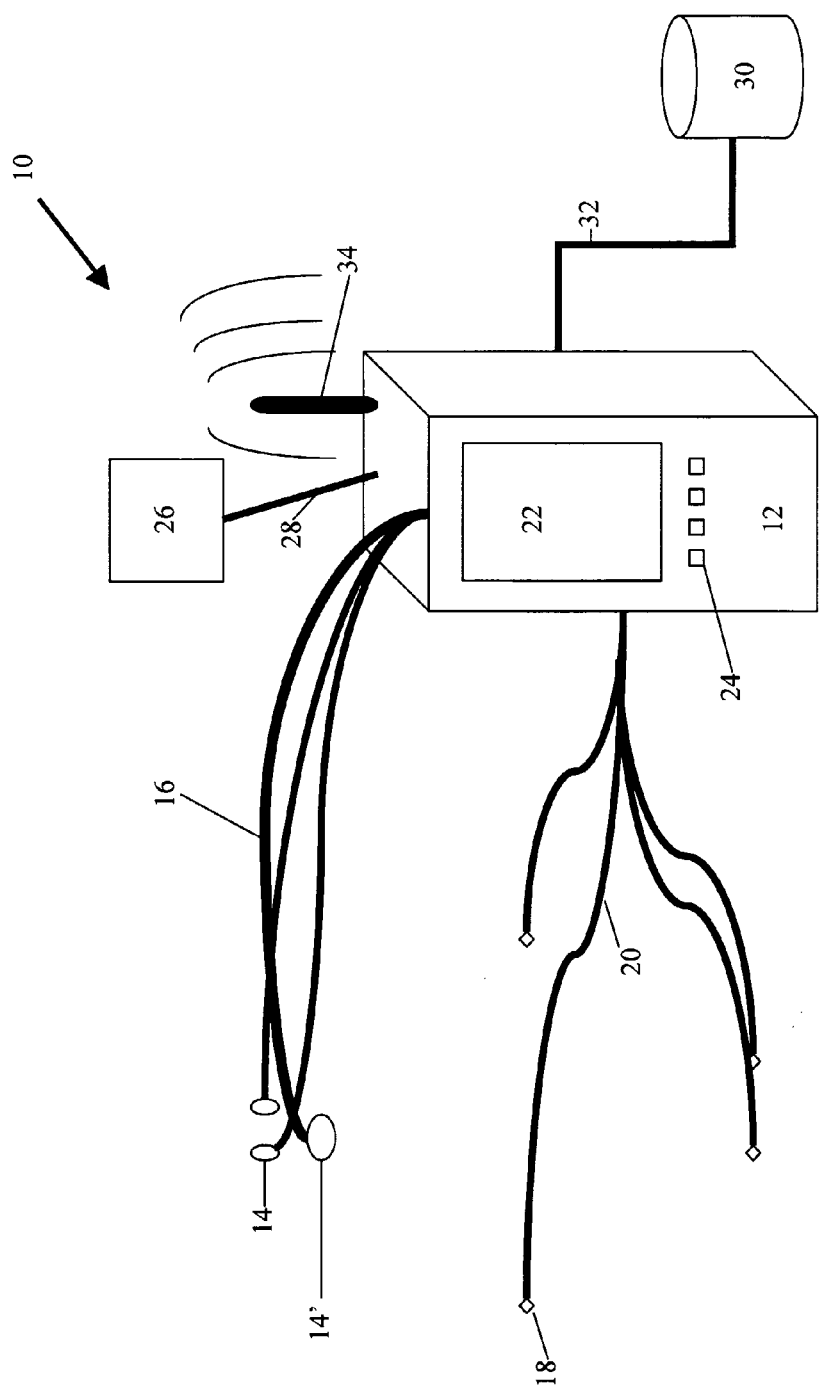
FIG. 1 is a schematic of an inventive system positioned in contact with a subject.

The present invention has utility in the detection and analysis of injuries to a subject as to whether neuronal injury is involved and thereby facilitating rapid treatment to ameliorate secondary neuronal injury associated with the event. In a preferred embodiment, the present invention is coupled to a subject by an emergency first responder and uses subject condition information to categorize the form of injury and begin a treatment regime on site to limit detrimental physiological responses to the injury. Wireless transmission of system data and dosing is optionally transmitted to a trauma center prior to transport of the subject.

The present invention provides a system and method for detecting, analyzing and then optionally ameliorating further injury to a subject's neurological system once that subject has suffered such an initial injury. The system provides detection and analysis support to classify such injury, and the method of the present invention includes selecting the correct neuroprotective pharmaceutical from a preexisting kit of such pharmaceuticals, and then delivering via a variety of means that pharmaceutical into the injured person.

The term "subject" means all animals including humans, examples of which include human and non-human subjects including cows, dogs, cats, goats, sheep, and pigs.

Those skilled in the art are easily able to identify subjects who have sustained neurological injuries including, but not limited to, conditions such as unconsciousness or inability to move.

According to the present invention, emitters are attached to a portion of a subject body. With emission of small amounts of electrical current from the emitter and through the subject body, neural conductivity is measured by a detector coupled to the subject. While it is appreciated that a single emitter and/or detector is operatively moved sequentially between a variety of extrema points illustratively including hand, wrist, forearm, upper arm, cervical region, abdominal region, waist, groin, thigh, calf and foot; in a preferred embodiment, a plurality of emitters are provided to continually monitor conductivity between an emitter and a signal detector. By measuring neuronal conductivity between a distal emitter and a detector in electrical communication with the central nervous system and comparing that measurement with known neuronal states, the nature of the injury a subject has experienced is communicated at the scene of the incident to a first responder. The known states are either contained within a database or calculated based on input data. In a preferred embodiment, the system also allows a first responder to manually enter subject conditional information such as age, sex, responsiveness to standard neurological physical examination tests and the like. More preferably, an inventive system also has a portal for receiving monitoring equipment signal input. The monitoring equipment illustratively including electrocardiogram, electroencephalogram, sphygmomanometer, blood oxygen meter and temperature. The monitoring of subject status is then analyzed to provide a first responder having a limited neurological training with a classification as to the type of neuronal injury a subject may have experienced. An inventive system is optionally programmed to provide instructions as to drug delivery at that point as well as possible recommendations for additional analyses, physical transport precautions or other suggested actions. In a simplified version, an inventive system upon providing a classification as to neuronal injury simply continues to log data and the first responder would seek instructions from a physician at a remote location as to immediate therapies to be provided.

The system and method of the present invention includes attaching emitters to pre-designated areas of the body, for example, but not limited to, an area of the ear which has a nerve which is bundled to the nerves running to muscle groups in the back of the calf, attaching sets of detectors to other areas of the body, for example, but not limited to, a muscle group in the back of the calf, and then emitting small amounts of electrical current into the emitter and determining if there is a complete circuit in the body; i.e., determining if there is such nerve damage that the signal cannot be detected as a result of the possible injury, as well as analyzing such signals against a database of such signals for the muscle group to determine the percentage of such signal strength compared to the norms of the database.

Placement of a current emission detector in electrical communication with the central nervous system can occur in a variety of locations depending on the physical condition of the subject. Detector coupling positions illustratively include the ear, jaw, temple and intravertebral. In a preferred embodiment, an emission detector is a spring-loaded disposable clip with needle-like prongs intended to reach the nerve nexus point. Alternatively, a disposable pad with a needle-like attachment pierces the subject's skin to attain electrical communication with a nerve nexus point and is adhesively held in position to receive neural conduction signals provided by the distal emitters. While the present invention has been detailed with respect to a distal electrical signal emission and a central nervous system detection, it is appreciated that the present invention is equally operative with central nervous system electrical current emissions and distal sensing.

Figure 2:
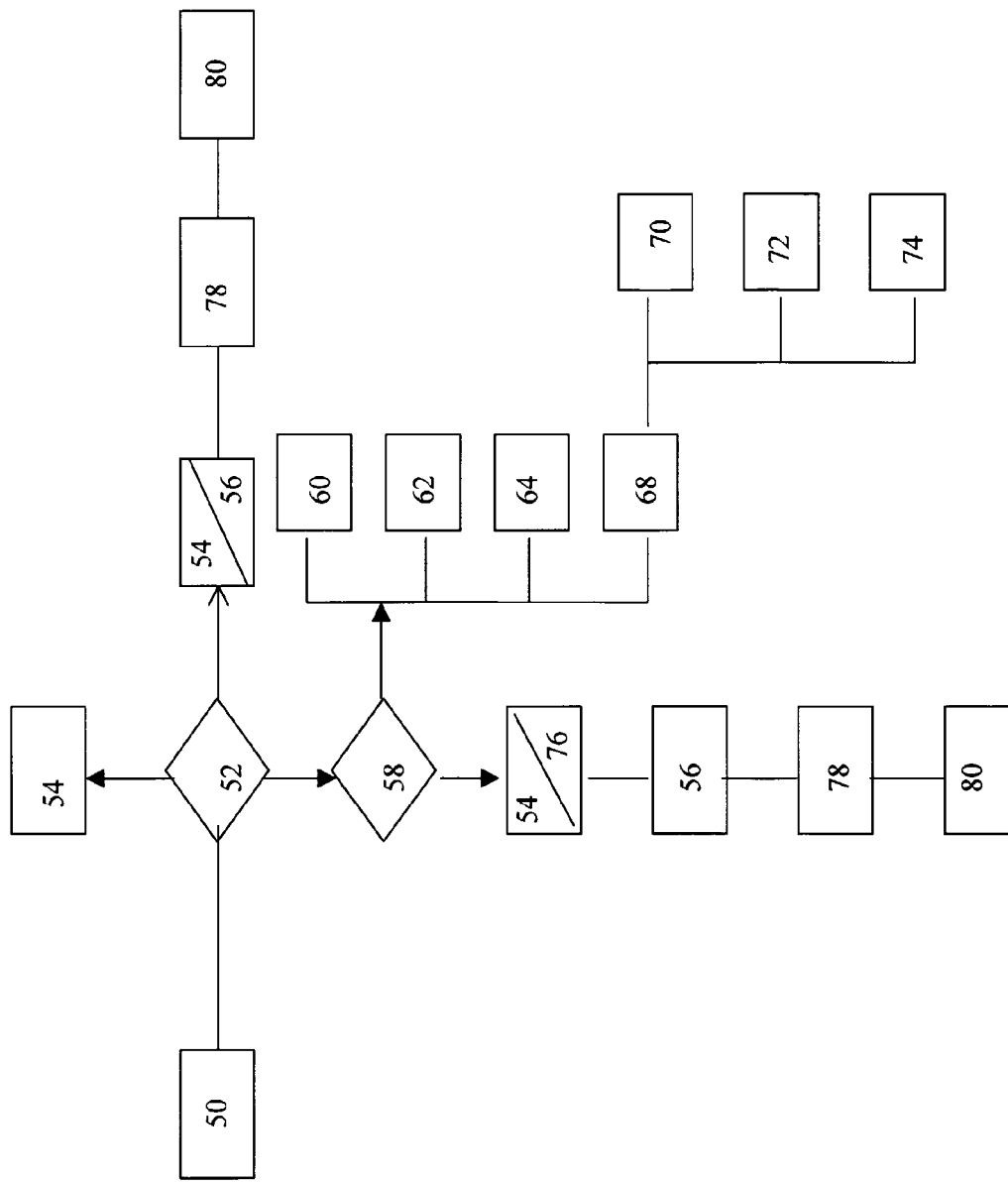
FIG. 2 is a schematic flowchart of the general operation of the inventive system depicted in FIG. 1.
Figure 3:
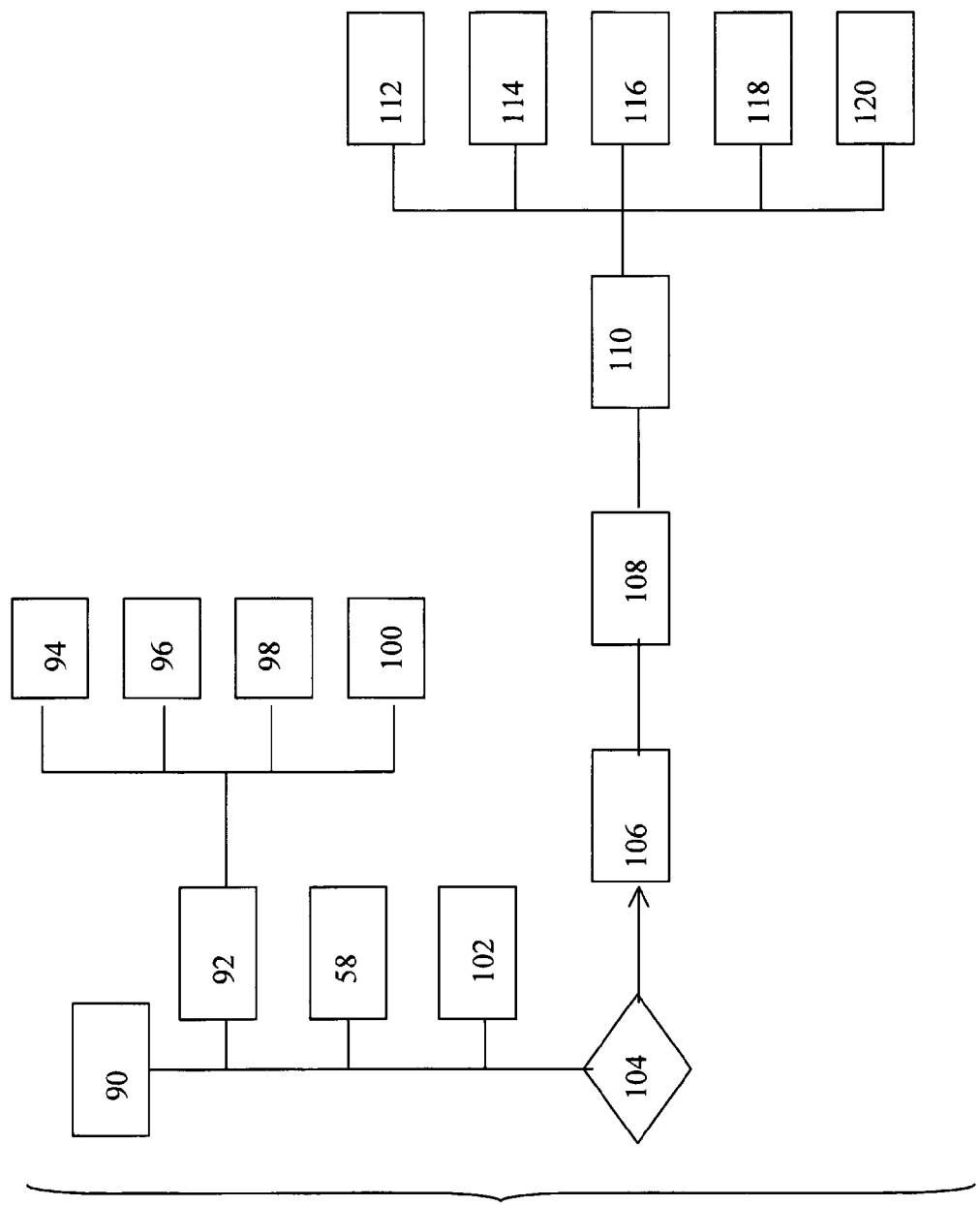
FIG. 3 is a schematic flowchart of an expert system analysis module depicted in FIG. 2.

The present invention is further detailed with regard to FIGS. 1-3 which represent non-limiting exemplary embodiments of the present invention. An inventive system is shown generally at 10 for field detection and analysis of potential neurological injury in a subject. The system 10 includes a computing device 12 having at least one signal emitter 14 or 14' attachable to a first position on a subject to emit an electrical signal generated by the computing device into the subject such that the electrical signal is communicated by emitter 14 to at least one nerve in proximity to the first position. As shown in FIG. 1, the at least one signal emitter is a spring-loaded ear clip. Emitter 14' is a skin patch emitter including a transdermal needle electrode driven into electrical communication with a nerve nexus point. Preferably, the emitters 14 and 14' are disposable and sterile. An emitter 14 or 14' is connected to a computing device by an electrically conductive wire 16. It is appreciated that in providing multiple emitters 14 and 14', a first responder is able to operate an inventive system regardless of the physical injuries sustained by a subject. The computing device 12 also is in electrical communication with at least one signal detector 18 attached to a second position on the subject to detect the electrical signal transmitted by way of the computing device 12 via wire 16 to the emitter 14 or 14' and through the subject nerves to the detector 18. The detector 18 being in electrical communication with the computing device by way of an electrically conductive wire 20. Preferably, as shown in FIG. 1, multiple detectors are provided. While the configuration depicted in FIG. 1 generically tests nerve conductivity to the four limbs of the subject, it is appreciated that multiple sensors are readily provided along the limb length of a suspected course of injury. Preferably, a detector 18 is a disposable adhesive sensor pad in electrical communication with the subject nervous system. The second position at which the detector 18 is positioned typically is in communication with the peripheral nervous system and it is appreciated that an inventive system is operative to detect and analyze conduction between various portions of the central nervous system. A detector 18 is operative as a topical adhesive pad or can be of a construction identical to an emitter 14 or 14'.

The computing device 12 also contains a processor circuit (not shown) for comparing a reference signal stored in a database with the detected electrical signal. The processor indicates neurological injury when the detected electrical signal is beyond a preselected range of the threshold reference signal. In a preferred embodiment, multiple reference signals are stored within the computing device database. Reference signals preferably are loaded into the database that relate to subject age, physical condition, pharmaceuticals present within the subject body, as well as references corresponding to different classifications of neural injury. A display 22 within the computing device 12 provides a first responder with an indication of the neurological status of the subject. Preferably, the computing device 12 includes a user interface 24 allowing a first responder to key in subject vital signs and information. Additionally, an inventive computing device 12 also receives an output signal from an ancillary monitoring device 26. The ancillary monitoring device 26 monitoring a subject conditional parameter. The output from monitoring device 26 to the computing device 12 being via a coupling 28. Monitoring device 26 illustratively including an electrocardiogram, an electroencephalogram, a sphygmomanometer, a cranial pressure monitor, a blood oxygen saturation monitor, and a thermometer. It is appreciated that manually keyed information and information provided by one or more ancillary monitoring devices 26 provides the processor of the computing device 12 with additional data that can be used to select threshold reference signals that more accurately reflect subject baseline status. Additionally, it is appreciated that a threshold reference signal need not be stored in a database but rather computed from a preloaded equation with input for the variable equation aspects being provided by sensors 18, user interface 24 and ancillary monitoring devices 26.

Preferably, the system 10 also includes a biochemical analyzer sampling a biological fluid obtained from the subject for the presence of chemical species or concentrations indicative of neurological injury. The biochemical analyzer 30 providing an output signal to the computing device 12 by way of a wire 32. Neuronal injury is known to create a cascade of cellular and chemical reactions based on the type of injury. Unfortunately, a number of these physiological responses, while useful in diagnosing a particular type of neuronal injury, lead to secondary injury. By way of example, immune cells are rarely found in an undamaged central nervous system, yet upon neuronal injury, immune cells tend to congregate in the region of injury. The presence of inflammation, oxidizing species, excess neurotransmitters and an influx of calcium ions into the region of injury have all been noted. Apoptosis of damaged neural cells has also been noted in animal subjects. Current theories as to the treatment of neurological injuries state that the quenching of oxidants, suppression of inflammation, excitotoxicity, apoptosis and calcium influx each alone or preferably in combination would improve recovery of neurological function following an injury. The biological analyzer 30 sampling for a chemical species or a concentration of otherwise common species indicative of neurological injury is therefore proposed. Conventional laboratory biochemical analyzers are operative in operation as a biochemical analyzer 30 according to the present invention. Preferably, the biochemical analyzer 30 regardless of the basis of analysis is modified to sacrifice resolution for durability associated with use in an ambulance or other first responder field setting. A biological fluid obtained from the subject suitable for analysis is one predetermined to be indicative of neurological condition. Biological fluids operative herein illustratively include blood, cerebrospinal fluid, saliva and urine. Preferably, both blood and cerebrospinal fluid chemistries are analyzed for immune cascade components.

Based on the various inputs, the computing device 12 provides a first responder with suggestions as to immediate interventive pharmaceutical treatments, physical transport precautions or other possible actions. A first responder carrying a pharmaceutical delivery kit containing the various drugs suitable for immediate use allows a first responder to intervene into the detrimental immune system response to the neurological injury thereby improving the likely clinical outcome.

In a preferred embodiment, computing device 12 includes a wireless transponder 34 communicating input data and computing device suggestions to a remote physician. The remote physician is able to review the suggested pharmaceutical intervention and override or modify the information appearing on the computing device display 22.

A flowchart of the general operation of an inventive system is depicted in FIG. 2. A first responder arrives to the scene of a subject injury incident 50. A first responder assesses the type of injury 52. If there is no neuronal injury, then the physical injury is treated 54. If a peripheral neural injury is noted, then the first responder treats the physical injury 54 and consults the expert neuronal injury analysis system 56. The expert system 56 is further detailed with respect to FIG. 3. In the event that the first responder classifies the injury as a central nervous system injury to the head or spinal cord, the injury is classified into one of a preselected set of central nervous system injury types with the help of an inventive system. The classification 58 illustratively includes classes as to visible traumatic injury 60, visible hemorrhagic injury 62, ischemic injury 64 associated with subject consciousness, confusion, loss of control of speech or limbs, or other abnormal neurological test functions. An additional class includes non-observable injuries 68. Non-observable injuries 68 are further classified based on the nature of the incident as to, for instance, anoxic 70 such as that associated with drowning, traumatic 72 as might be experienced in a vehicle crash or other force-induced trauma, and nonspecific 74. Upon classifying the central nervous system injury, physical injuries 54 are treated and a two-part analysis is performed 76 including neurocontinuity testing through the use of passing electrical current through a subject nervous system to detect discontinuities or decreased conduction values. A second part of the analysis includes blood marker sampling and injury chemical analysis. The second part of the analysis includes biological fluid sampling and injury associated chemical analysis being performed. It is appreciated that sampling can include multiple biological fluids such as blood and cerebrospinal fluid. Based on the analysis 76, the expert system 56 is consulted to provide recommendations as to the pharmaceutical interventions to be pursued at the scene of the incident as well as during transport to a trauma center and thereafter. As secondary injury associated with neurotrauma is most pronounced in the first ten minutes after injury, treatment regimens in the first ten minutes, thirty minutes, hour, four hours and thereafter are appreciated to be variable to suppress to the greatest possible extent the secondary neuronal injury. The expert system 56 provides the first responder with suggested pharmaceutical intervention protocols 78 and communicates the protocols 78 to a remote physician 80 in order to provide verification.

The steps performed by the expert neurological injury system analysis module 56 are shown in greater detail with respect to FIG. 3. Information capture 90 includes the input of information either provided through manual entry by a first responder or from an auxiliary monitoring device coupled to an inventive system. Information includes patient physical condition 92. Patient physical condition includes an input as to the consciousness status of the subject 94, blood pressure and/or heart rate 96, the presence of visible injuries and the specification of those injuries 98 and input as to the incident type 100 into categories illustratively including vehicle accident, fall, drowning or the like. Central nervous system injury classification 58, if present, is also provided. Information capture 90 also preferably includes inputs as to physical treatment actions taken and medications present within the subject's system 102. Based on the information capture 90, the computing device determines the appropriate test parameters 104 and instructs the first responder through each additional needed examination 106. The first responder then inputs additional required information and compares the input information and information capture against at least one reference value that is either computed based on an equation stored within the computing device or stored within a database 108. The expert system then suggests to a first responder therapeutic protocols 110. Illustrative therapeutic protocols 110 include intravenous single drug or cocktails from a preset tray 112, cerebrospinal fluid injectable single drug or cocktails from a preset tray 114, additional analyses or physical parameter collection 116, physical transport precautions 118, or other suggested actions.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

Any patents, applications or publications mentioned in the specification are indicative of the levels of those skilled in the art to which the invention pertains. These patents, applications and publications are herein incorporated by reference to the same extent as if each individual publication was specifically and individually indicated to be incorporated by reference.

The invention claimed is:

1. A system for detecting a neurological injury in a subject prior to transport from a site of the injury, said system comprising:
a computing device comprising:
at least one distal signal emitter attachable to a first position on the subject to emit an electrical signal generated by the computing device into the subject such that the electrical signal is communicated to a nerve in proximity to the first position;
at least one signal detector attachable to a second position in electrical communication with a subject central nervous system on the subject to detect the electrical signal transmitted by the nerve as neural conductivity as a detected electrical signal; and
a processor for comparing a threshold reference value with the detected electrical signal and indicating the neurological injury when the detected electrical signal is beyond a preselected range of the reference value; and
a biochemical analyzer for analyzing fluid samples for the presence of chemical species or concentrations indicative of the neurological injury providing an output signal to said computing device; and
a display providing indication of the neurological injury associated with the output signal and the detected electrical signal;
said system providing suggestions as to at least one of: immediate interventive neuroprotective pharmaceutical treatments, or physical transport precautions prior to transport from a site of the injury.

2. The system of claim 1 wherein a database is comprised of signal strengths for various positions and muscle groups of the subject.

3. The system of claim 1 wherein the computing device provides a user with instruction for positioning the at least one emitter and the at least one detector on the subject.

4. The system of claim 1 further comprising an ancillary monitoring device providing the computing device with an input relating to a physiological parameter of the subject.

5. The system of claim 1 further comprising a user interface for data input to the computing device.

6. The system of claim 4 further comprising a wireless transmitter coupled to the computing device communicating the indication of neurological injury and input.

7. The system of claim 1 wherein the computing device provides suggested neuroprotective pharmaceutical treatment protocols for the subject.

8. The system of claim 1 in combination with a kit of neurologically active neuroprotective pharmaceuticals and at least one device for introducing a pharmaceutical into the subject.

9. A process for detecting a neurological injury in a subject comprising:
attaching a distal emitter at a first position and a detector at a second position to the subject in electrical communication with a subject central nervous system prior to transport of the subject to a trauma center;
emitting an electrical signal from a computing device into the subject at the first position via the emitter;
detecting the electrical signal transmitted by a nerve at the second position with the detector as neural conductivity;
comparing the detected electrical signal with a threshold reference value in the computing device;
using a biochemical analyzer to analyze fluid samples obtained from the subject for the presence of chemical species or concentrations indicative of the neurological injury to create an output signal;
indicating the neurological injury when the detected electrical signal is beyond a preselected range of the reference value of and the output signal corresponds to the presence of chemical species or concentrations indicative of the neurological injury; and
providing suggestions as to at least one of: immediate interventive neuroprotective pharmaceutical treatments, physical transport precautions, or other possible action.

10. The process of claim 9 further comprising communicating at least one of the detected electrical signal or indicated neurological injury to a remote location.

11. The process of claim 9 further comprising instructing a user to perform physical examination on the subject to obtain information and providing the information to said computing device.

* * * * *